(12) United States Patent
Andreis et al.

(10) Patent No.: US 10,071,236 B2
(45) Date of Patent: Sep. 11, 2018

(54) TOTAL ISOLATION DIVERTER VALVE

(71) Applicant: DOLPHIN FLUIDICS S.R.L., Corsico (MI) (IT)

(72) Inventors: Diego Andreis, Milan (IT); Francesco Butera, Arese (IT)

(73) Assignee: DOLPHIN FLUIDICS S.R.L., Corsico (MI) (IT)

( * ) Notice: Subject to any disclaimer, the term of this patent is extended or adjusted under 35 U.S.C. 154(b) by 14 days.

(21) Appl. No.: 15/292,474

(22) Filed: Oct. 13, 2016

(65) Prior Publication Data

US 2017/0108020 A1     Apr. 20, 2017

(30) Foreign Application Priority Data

Oct. 15, 2015   (IT) .................. 102015000061915

(51) Int. Cl.
    *A61M 39/00*      (2006.01)
    *A61M 39/22*      (2006.01)
    (Continued)

(52) U.S. Cl.
    CPC ........... *A61M 39/223* (2013.01); *F15B 21/12* (2013.01); *F15C 1/08* (2013.01); *F15C 1/143* (2013.01);
    (Continued)

(58) Field of Classification Search
    CPC ........ A61M 39/223; A61M 2205/0266; A61M 16/20; F15C 1/143; F15C 1/08;
    (Continued)

(56) References Cited

U.S. PATENT DOCUMENTS 3,452,769 A * 7/1969 Fidler ................. F15C 1/04
                                                    137/829
3,463,177 A * 8/1969 McMillan ............. F15C 1/04
                                                    137/828
(Continued)

FOREIGN PATENT DOCUMENTS

EP          0085298 A1      8/1983
EP          0126608 A1     11/1984
(Continued)

*Primary Examiner* — Eric Keasel
(74) *Attorney, Agent, or Firm* — King & Schickli, PLLC

(57) ABSTRACT

The invention describes a total isolation diverter valve comprising a valve body whereon a main inlet conduit for inletting a fluid, a first outlet conduit for outletting the fluid and at least one second outlet conduit for outletting the fluid are obtained. The first outlet conduit for outletting the fluid is provided with a first fluid adhesion inner surface and the second fluid outlet conduit is provided with a second fluid adhesion inner surface. Between the main fluid inlet conduit and the two fluid outlet conduits a connection channel is interposed. On the connection channel at least one device for perturbing at least one of the first fluid adhesion inner surface and the second fluid adhesion inner surface is provided. The perturbation device is configured so as to cause a deviation of the fluid flow from the first fluid outlet conduit to the second fluid outlet conduit or vice-versa by exploiting a physical effect called Coandă effect. The perturbation device comprises at least one perturbation orifice, which faces the first fluid adhesion inner surface, and at least one opening/closing element, configured for opening and sealingly closing a respective perturbation orifice.

18 Claims, 7 Drawing Sheets

(51) Int. Cl.
*F15D 1/02* (2006.01)
*F15D 1/06* (2006.01)
*F15B 21/12* (2006.01)
*F15C 1/08* (2006.01)
*F15C 1/14* (2006.01)
*A61M 16/20* (2006.01)

(52) U.S. Cl.
CPC ................ *F15D 1/02* (2013.01); *F15D 1/06* (2013.01); *A61M 16/20* (2013.01); *A61M 2205/0266* (2013.01)

(58) Field of Classification Search
CPC ... F15B 21/12; F15D 1/06; F15D 1/02; Y10T 137/2164; Y10T 137/2169; Y10T 137/2174; Y10T 137/2202; Y10T 137/2218; Y10T 137/2245; Y10T 137/2251
USPC ........ 137/822, 823, 824, 829, 832, 837, 838
See application file for complete search history.

(56) References Cited

U.S. PATENT DOCUMENTS

| | | | | |
|---|---|---|---|---|
| 3,486,517 | A * | 12/1969 | Gaura | F15C 1/08 137/832 |
| RE27,087 | E * | 3/1971 | Binder | F02M 7/106 137/832 |
| 3,608,573 | A * | 9/1971 | Bahrton | F15C 1/08 137/839 |
| 4,278,110 | A | 7/1981 | Price et al. | |
| 4,549,574 | A * | 10/1985 | Taylor | F15C 1/08 137/803 |
| 6,389,798 | B1 * | 5/2002 | Tilston | F15C 1/08 60/39.23 |
| 8,387,662 | B2 * | 3/2013 | Dykstra | E21B 34/08 137/813 |
| 2012/0255739 | A1 | 10/2012 | Fripp et al. | |

FOREIGN PATENT DOCUMENTS

| | | |
|---|---|---|
| GB | 1214081 A | 12/1970 |
| JP | 2005121209 A | 5/2005 |
| WO | 8202076 A1 | 6/1982 |

* cited by examiner

TOTAL ISOLATION DIVERTER VALVE

FIELD OF THE INVENTION

The present invention refers to a so-called total isolation valve, in particular a total isolation diverter valve of the three-way type.

BACKGROUND OF THE INVENTION

The total isolation valves, especially in three-way diverter configuration, combine the characteristics of strength and reliability with constructive solutions that make them particularly suitable for controlling aggressive and/or incontaminable fluids. The fluid comes into contact with the valve body and the sealing device only, wherein the sealing device typically consists of a membrane or a separating lever. This solution preserves the fluid from contamination, which can alter the chemical-physical characteristics thereof, and from excessive thermal shocks. The total isolation valves are thus suitable for applications in the food, biotechnology, chemical-pharmaceutical and physiological-medical sectors.

A known embodiment of a total isolation valve, in particular of the three-way type, is shown in FIG. 1. The valve, wholly indicated with reference numeral 100, is provided with a valve body 102 inside which a fluid is made to flow. Inside the valve body 102 there is a lever shutter 104 actuated by a magnetic drive solenoid 106. The movement of the lever shutter 104 is driven through a series of levers 108 and transmissions 110 that make the construction of the valve 100 complicated.

In addition, the total isolation valves provided with isolation lever require a particular configuration of the inlet and outlet conduits of the valve, consequently limiting the design freedom of the fluidic part of the valve itself. Indeed, in the three-way configuration the most common constructive choice, if not the only one, is to provide an isolation lever or a double membrane.

The constraints linked to the actuation also have an impact on the internal constructive geometries of the valve, complicating the design thereof at the expense of cleanliness and hygiene of the valve itself. This drawback is even more critical if one considers the typical applications in the biomedical or "food and beverage" technical fields.

Another example of a total isolation valve according to the prior art is described in document EP 0 085 298 A1. Also in this configuration of the valve, however, it should be highlighted how the constructive complexity both of the fluidic part, and of the actuation part is high in order to ensure the total isolation function. In the valve illustrated in document EP 0 085 298 A1 the conduits and the sealing areas, which through the opening and closing of pistons establish the direction of the flow, have critical areas in terms of hygiene. The conduits themselves have sudden changes of direction (angles at 90° and 180°) which do not promote normal flow of the fluid and thus increase the load losses of the valve.

Further examples of valves or devices for controlling the direction of the flow of a fluid are described, for example, in documents U.S. Pat. No. 4,278,110 A, GB 1 214 081 A, JP 2005-121209 A, WO 82/02076 A1, EP 0 126 608 A1 and US 2012/255739 A1.

The general purpose of the present invention is therefore to make a total isolation valve, in particular a total isolation diverter valve of the three-way type, which is capable of solving the aforementioned drawbacks of the prior art in an extremely simple, cost-effective and particularly functional manner.

SUMMARY OF THE INVENTION

In detail, a purpose of the present invention is to make a total isolation diverter valve that ensures absolute hygiene, since the main conduits engaged by the fluids are not provided with any additional component necessary for the diversion of the flow or, in other words, the valve is completely "empty" on the inside.

Another purpose of the present invention is to make a total isolation diverter valve that has the ability to manage high hydraulic powers with very low actuation forces.

Another purpose of the present invention is to make a total isolation diverter valve that makes it possible to obtain high diverting speeds of the flow, particularly in the case of high hydraulic powers.

Another purpose of the present invention is to make a total isolation diverter valve that is reliable, since the diversion of the main flow, even for high hydraulic powers, is linked only to a physical effect and not to additional mechanisms and/or devices like levers, pistons or dividing walls that could over time be subject to wear or malfunction.

Another purpose of the present invention is to make a total isolation diverter valve that makes it possible to minimize the size and the weight of the valve itself even for the management of high hydraulic powers.

Yet another purpose of the present invention is to make a total isolation diverter valve that makes it possible to indirectly obtain, in addition to the diverting of the flow, a mixing between a liquid and air, so as to be able to be used effectively, for example, in the beverage industry to prepare emulsified beverages like cappuccino.

These purposes according to the present invention are accomplished by making a total isolation valve, in particular a total isolation diverter valve of the three-way type, as outlined in claim 1.

Further characteristics of the invention are highlighted by the dependent claims, which are in integral part of the present description.

The total isolation diverter valve according to the present invention has been designed in particular but not exclusively for all technical fields in which it is necessary to maintain high hygiene standards, intrinsic reliability of the valve itself and considerable reduction of the size, weight and electrical power involved. The total isolation diverter valve according to the present invention is provided with an improved fluidic part for these technical fields, where high standards of hygiene and "self-cleaning" are required, as well as with high performance in terms of working pressures and flow rates. The actuator part, outside of the fluidic body, can also consist of an element manufactured with a shape-memory alloy (SMA) that ensures numerous advantages, such as a big reduction in size and weight, low energy consumption, absolute silence, reliability and precision.

The fluidic part per se constitutes a novel element since it is geometrically studied to ensure the diversion of the flow through the exploitation of a physical effect called "Coandă effect". The Coandă effect is the tendency of a jet of fluid to follow the outline of a nearby surface. The phenomenon is named after the Romanian pioneer of aerodynamics Henri Coandă, who patented in 1936, first in France and then in the USA, some instruments that exploited the property of diverting a jet. Until today, the Coandă effect has mainly been applied in the aeronautical field through different studies aimed at developing aircraft with particular profiles. The advantage of these aircrafts consists of their maneuverability and their ability to spin in the air. A practical example of this application is found in the Antonov An-72 aircraft, in which the particular positioning of the engines was specially studied to exploit the Coandă effect. The Coandă effect was also used in Formula 1, for a few years and until 2013, through special bodywork shapes capable of directing the flow of hot air coming from the exhausts at the sides of the rear extractor profile, creating a sort of aerodynamic "seal" useful for increasing the efficiency of the extractor itself and therefore the aerodynamic load.

From a physical/mathematical point of view, however, the Coandă effect applies to a generic fluid and therefore is not limited to air. The explanation of the phenomenon, indeed, derives from the fact that the fluid, moving along a surface, causes friction that tends to make it slow down. The resistance to movement of the fluid is however applied only to the particles of fluid immediately in contact with the surface. The outer particles of fluid, due to the molecular interactions that tend to keep them joined to the inner ones, will therefore change direction towards the inner fluid particles due to the difference in speed, thus making the fluid adhere to the surface.

Consequently, since the Coandă effect is linked to a friction phenomenon between fluid and wall, in the case of applications with liquids the adhesion forces involved are much greater than those that occur with air. It is thus possible to divert large flows even in conditions of high flow rates/pressures by simply suitably designing the geometries of the conduits of the valve. The act of diverting the flow is simply triggered by a perturbation of the main adhesion surface of a given conduit. This makes it possible to make the flow adhere to a second surface that belongs to a different conduit.

For this reason, the forces involved in the diverting of the flow are minimal, because they must only establish a perturbation of the adhesion surface and thus involve extremely low actuation forces, with relative practically negligible electrical consumption with respect to the hydraulic power that can be managed. Added to this is the suitability of causing this perturbation through an actuator manufactured at least partially with a shape memory alloy, with all of the further advantages that derive therefrom in terms of compactness, ease of integration, low consumption and precision of control.

BRIEF DESCRIPTION OF THE DRAWING FIGURES

The characteristics and advantages of a total isolation diverter valve according to the present invention will become clearer from the following description, given as a non-limiting example, referring to the attached schematic drawings, in which.

Detailed Description of the Invention

Figure 1:
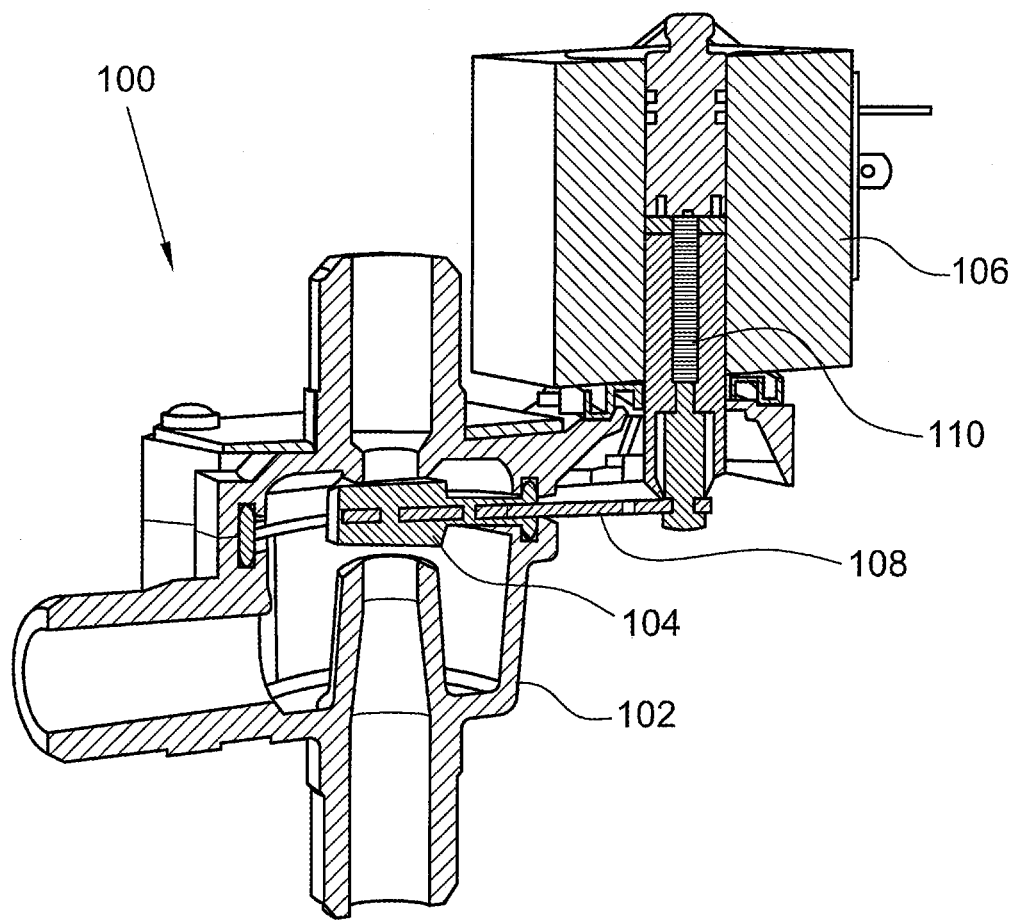
FIG. 1 is a schematic view of a known total isolation valve.

With reference in particular to FIGS. 2 to 7, some preferred embodiments of a total isolation diverter valve according to the present invention are shown. The valve comprises a valve body 10 whereon a main fluid inlet conduit 12 and at least two fluid outlet conduits 14, 16 are formed. In the embodiments illustrated in the figures the valve is of the three-way type. Indeed, there is a first fluid outlet conduit 14 and a second fluid outlet conduit 16.

Each inlet 12 and outlet 14, 16 conduit is provided with a respective inner surface 18, 20 and 22 on which the fluid adheres in passing from such a fluid inlet conduit 12 to at least one of the fluid outlet conduits 14, 16. In detail, the fluid inlet conduit 12 is provided with its own inner fluid adhesion surface 18, the first fluid outlet conduit 14 is provided with a first fluid adhesion inner surface 20, or main or preferential adhesion surface, and the second fluid outlet conduit 16 is provided with a second fluid adhesion inner surface 22, or secondary adhesion surface.

On a connection channel 24 interposed between the fluid inlet conduit 12 and the fluid outlet conduits 14, 16 at least one device for perturbing at least one of the first fluid adhesion inner surface 20 and the second fluid adhesion inner surface 22 is obtained. The perturbation device is configured to cause a diversion of the fluid flow from the first fluid outlet conduit 14 to the second fluid outlet conduit 16 or vice-versa by exploiting a physical effect called Coandă effect.

Figure 2:
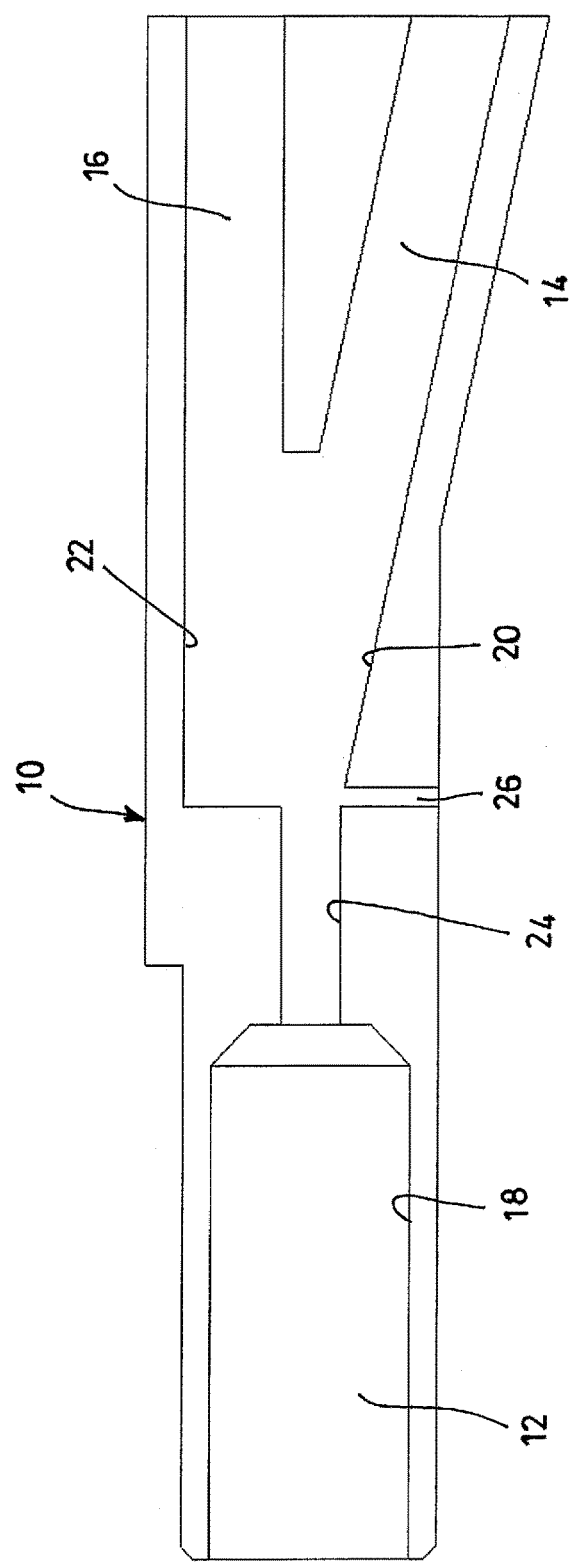
FIG. 2 is a schematic view of a first embodiment of the fluidic part of a total isolation diverter valve according to the present invention.

The operation of the total isolation valve shown in FIG. 2 is therefore that of a typical three-way diverter valve that has the task of placing the fluid inlet duct 12 in communication alternately with one of the first fluid outlet conduit 14 and the second fluid outlet conduit 16. In normal conditions the valve has a preferential operating state wherein the first fluid adhesion inner surface 20 of the first fluid outlet conduit 14 is involved. In other words, the fluid, by Coandă effect, will tend to follow the main or preferential adhesion surface 20. The valve is therefore normally open towards the first fluid outlet conduit 14.

As soon as a perturbation of the first fluid adhesion inner surface 20 occurs, caused by the perturbation device that in the embodiment of FIG. 2 comprises at least one perturbation orifice 26 that faces such a first fluid adhesion inner surface 20, the flow loses the adhesion to the first fluid adhesion inner surface 20 and is "drawn" towards the second fluid adhesion inner surface 22 of the second fluid outlet conduit 16. In this state the fluid will come out from the second fluid outlet conduit 16. The fluid will remain in this state as long as the perturbation caused by the perturbation device lasts. Preferably, the perturbation orifice 26 is interposed between the connection channel 24 and the first fluid outlet conduit 14 and develops along a direction substantially perpendicular to the direction of development of the connection channel 24.

At the moment when the perturbation stops, the fluid will go back to adhering to its main or preferential surface 20. Of course, the operation of the valve is closely linked to the geometric sizing and the shape of the fluid inlet 12 and outlet 14, 16 conduits in order to establish, at the deviation area of the flow, the correct physical conditions adapted for obtaining the Coandă effect.

In the configuration of the total isolation valve shown in FIG. 2 a monostable operation of said valve is provided, with a normally open preferential way ensured by the non-symmetrical geometry of the valve. It is possible to foresee a different configuration in which the behavior of the valve is bistable, as shown in the embodiment of FIG. 3.

Figure 3:
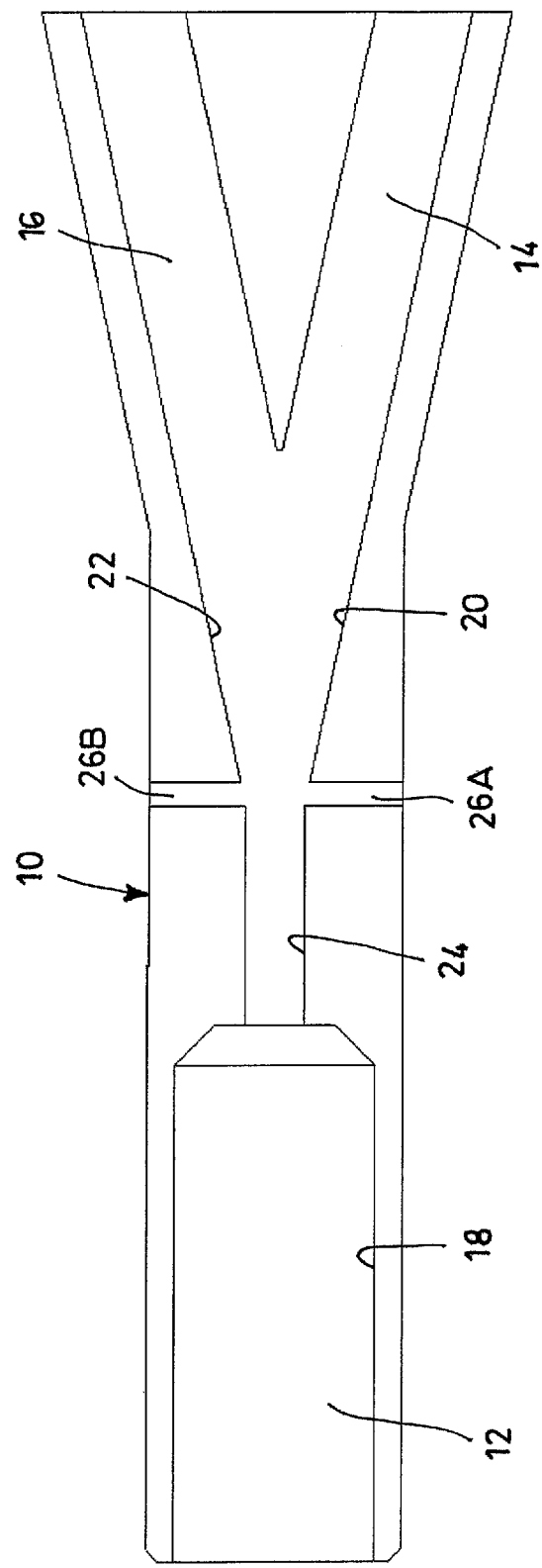
FIG. 3 is a schematic view of a second embodiment of the fluidic part of a total isolation diverter valve according to the present invention.

The valve of FIG. 3 comprises a valve body 10 whereon a first fluid outlet conduit 14 and a second fluid outlet conduit 16 are formed symmetrically with respect to the middle plane of such a valve body 10. The first fluid outlet conduit 14 and the second fluid outlet conduit 16 also have the same fluid passage section, as well as the same geometry.

In the embodiment of FIG. 3 the perturbation device comprises a pair of perturbation orifices 26A and 26B. A first perturbation orifice 26A is interposed between the connection channel 24 and the first fluid outlet conduit 14 and faces the first fluid adhesion inner surface 20, whereas the second perturbation orifice 26B is interposed between the connection channel 24 and the second fluid outlet conduit 16 and faces the second fluid adhesion inner surface 22. Both of the perturbation orifices 26A and 26B develop along a direction substantially perpendicular to the direction of development of the connection channel 24 and are arranged along the same axis.

In this case there is no preferential adhesion surface for the fluid and the flow remains in adhesion to the respective adhesion surfaces 20 and 22 until it is perturbed respectively through the first perturbation orifice 26A and the second perturbation orifice 26B. At the moment when the perturbation takes place, the flow diverts towards the opposite surface and stays there. The perturbation is therefore not permanent, but is interrupted immediately after the change of state according to the typical bistable behavior of a valve like that of FIG. 3.

Figure 4:
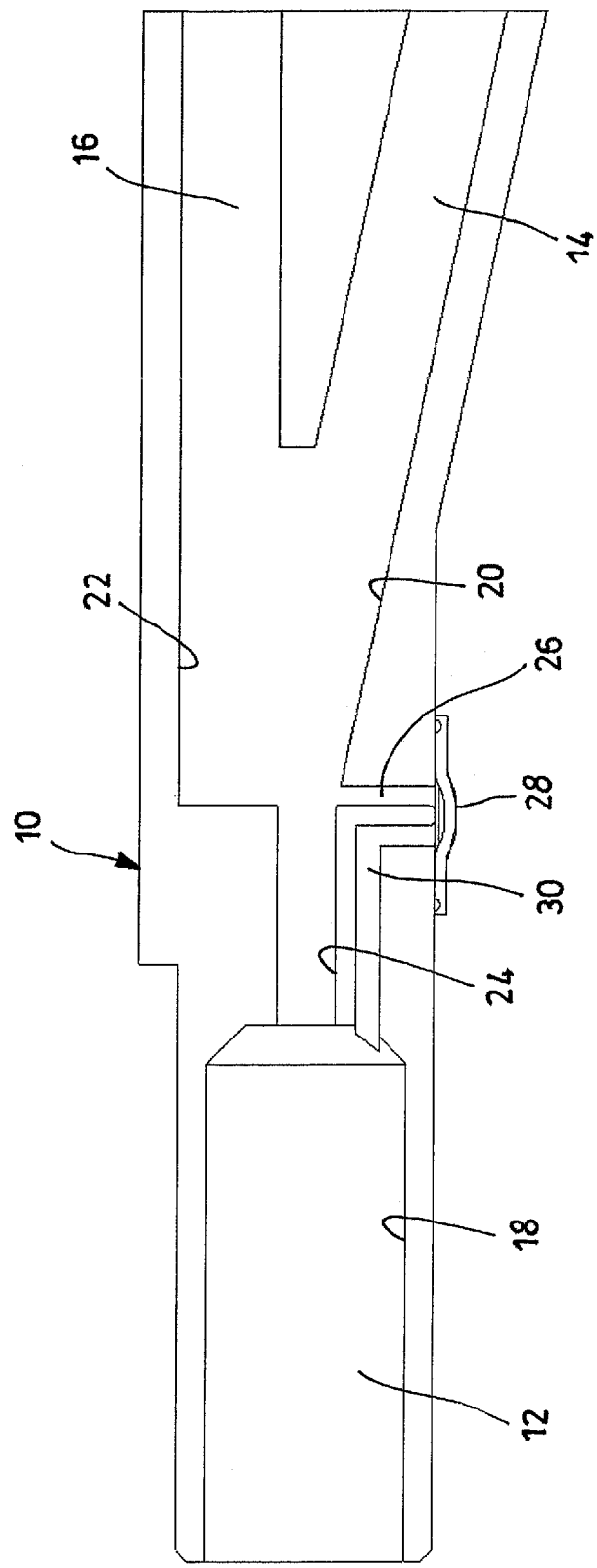
FIG. 4 is a schematic view of a first variant of the embodiment of FIG. 2.

FIG. 4 shows a first variant of the embodiment of FIG. 2, in which there is a possible mode of perturbation applied to the monostable valve. The perturbation device of the valve comprises at least one opening/closing element 28, configured to open and sealingly close a respective perturbation orifice 26. The opening/closing element 28 consists of an isolation membrane 28 manufactured with an elastic material.

The perturbation device of the valve also comprises at least one secondary inlet conduit 30 for a perturbation fluid, interposed between the main fluid inlet conduit 12 and a respective isolation membrane 28. The secondary inlet conduit 30 of the perturbation fluid is selectively placed in fluid communication with a respective perturbation orifice 26 through the respective isolation membrane 28.

In this first variant a minimal part of the fluid coming from the main fluid inlet conduit 12 passes, under pressure, through the secondary inlet conduit 30 and flows through the respective perturbation orifice 26, so as to generate a perturbation of the flow through the actuation of the respective isolation membrane 28. The isolation membrane 28 thus has the purpose of placing the secondary inlet conduit 30 in selective and controlled communication with the perturbation orifice 26. At the same time the isolation membrane 28 has the function of separating the fluidic part of the valve from the actuation part, which acts on the isolation membrane 28 itself. The pressurized fluid, which passes first through the secondary inlet conduit 30 and then through the perturbation orifice 26, perturbs the first fluid adhesion inner surface 20 managing to divert the main flow towards the second fluid adhesion inner surface 22. At the moment when the isolation membrane 28, through external actuation, interrupts the communication of the secondary inlet conduit 30 with the perturbation orifice 26, the perturbation stops and the flow goes back to adhering to the main or preferential adhesion surface 20 of the first fluid outlet conduit 14.

Figure 5:
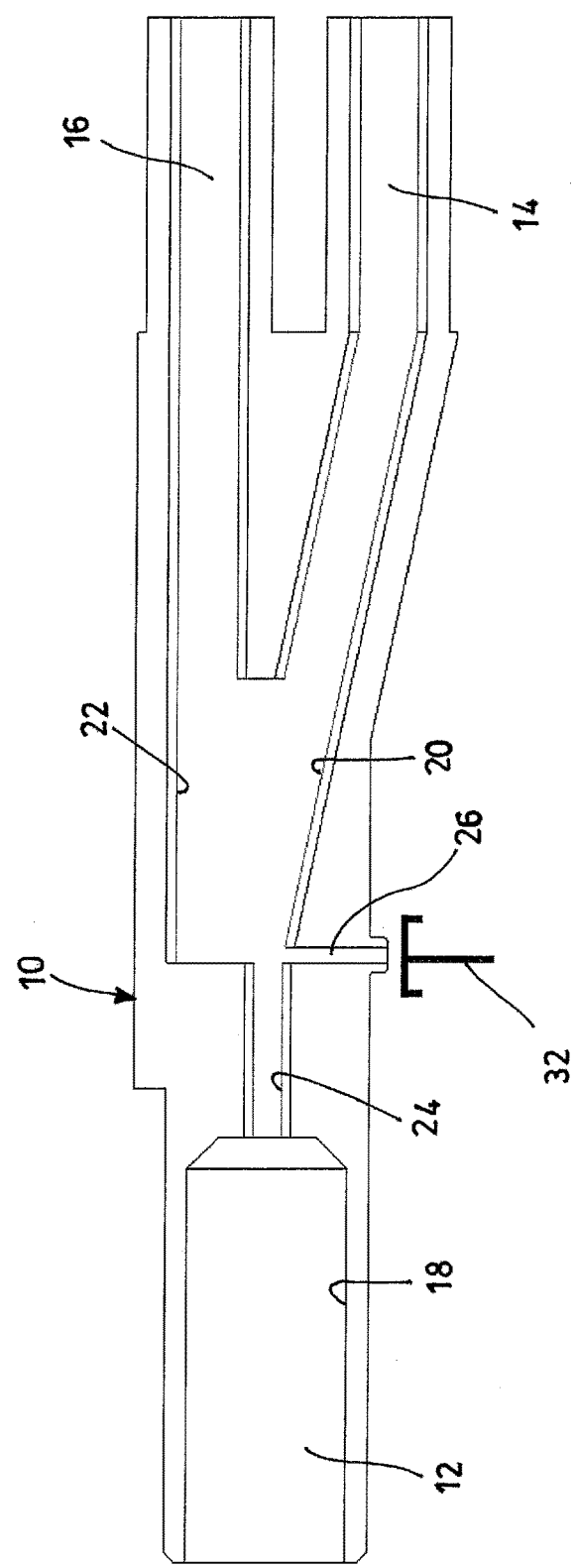
FIG. 5 is a schematic view of a second variant of the embodiment of FIG. 2.

FIG. 5 shows a second variant of the embodiment of FIG. 2, in which a second mode of perturbation is provided applied to the monostable valve. This second mode of perturbation is particularly advantageous in the case in which the fluid to be diverted is a liquid. The perturbation device of the valve comprises at least one opening/closing element 32 configured to open and sealingly close a respective perturbation orifice 26. The opening/closing element 32 consists of a plate movable with reciprocating motion along the direction of development of the respective perturbation orifice 26.

In this second variant, the main fluid (liquid) flow is perturbed simply by a flow of air that comes from outside of the valve through the perturbation orifice 26 when the respective plate 32 is in open configuration. In normal conditions the plate 32 keeps the perturbation orifice 26 closed. The fluid travels along the main or preferential adhesion surface 20 and comes out through the first fluid outlet conduit 14. At the moment when, through external actuation, intervention is carried out on the plate 32, the perturbation orifice 26 is placed in communication with the outside. Through the effect of the passage of the liquid, thanks to the Venturi effect, air is drawn inside the perturbation orifice 26, creating a flow of air that perturbs the adhesion of the fluid to the first fluid adhesion inner surface 20. The main flow thus deviates towards the second fluid adhesion inner surface 22. With the reclosure of the plate 32 the initial configuration of the valve is restored.

Figure 6:
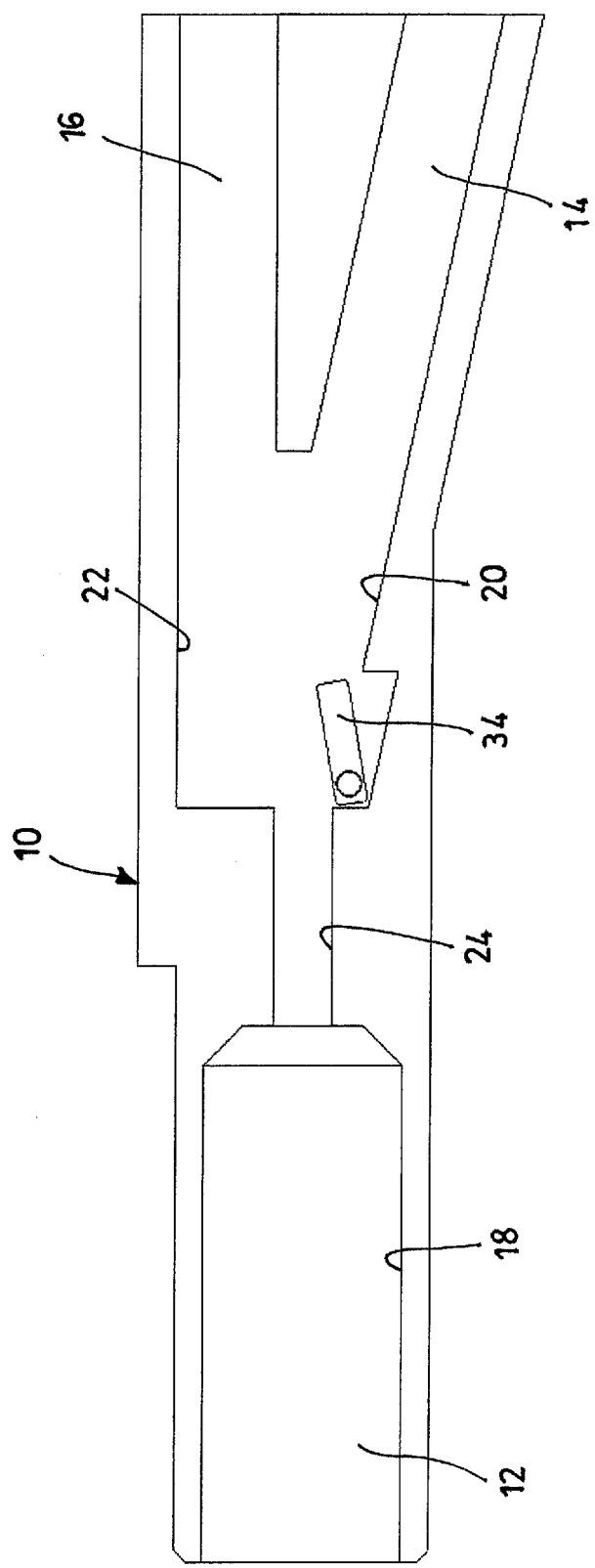
FIG. 6 is a schematic view of a third embodiment of the fluidic part of a total isolation diverter valve.

As shown in FIG. 6, a last mode of perturbation of the flow of fluid inside the valve body 10 can be carried out by acting directly on the geometry of at least one of the first fluid adhesion inner surface 20 and the second fluid adhesion inner surface 22. The perturbation device is thus provided with at least one mobile wall 34 interposed between the connection channel 24 and at least one of the first fluid adhesion inner surface 20 and the second fluid adhesion inner surface 22.

In a first normal or non-operative condition, the mobile wall 34 is lowered and its operative surface constitutes a part of the respective fluid adhesion inner surface 20. The fluid travels along the main or preferential adhesion surface 20 and comes out through the first fluid outlet conduit 14. In a second operative condition, a movement of the mobile wall 34, like for example the lifting shown in FIG. 6, forms a discontinuity on the respective fluid adhesion inner surface 20, causing a perturbation of the flow that thus deviates towards the other fluid adhesion inner surface 22.

The step of deviation of the fluid flow from the first fluid outlet conduit 14 to the second fluid outlet conduit 16 or vice-versa can also be controlled proportionally. In other words, it may be possible to partially and progressively deviate the amount of fluid from the first fluid outlet conduit 14 to the second fluid outlet conduit 16 or vice-versa.

The proportional control of the deviation of the fluid flow can be obtained through partialization of the perturbation. For example, with reference to the embodiment of FIG. 4, it is possible to partialize the perturbation flow that flows in the perturbation orifice 26 through the proportional control of the opening of the isolation membrane 28. Indeed, in order to obtain a complete deviation of the flow from the main adhesion surface 20 towards the secondary adhesion surface 22 it is necessary for the perturbation "signal" caused by the secondary flow, that flows firstly through the secondary inlet conduit 30 and then through the perturbation orifice 26, to exceed a predetermined minimum flow rate value. For lower flow rate values only a partial deviation of the main flow is obtained, which is in relation to the perturbation flow rate.

The proportional control of the deviation of the fluid flow can also be obtained by changing the geometry of the second fluid outlet conduit 16. For example, it is possible to introduce a mechanism for moving the second fluid adhesion inner surface 22, which in this case becomes mobile. Indeed, by moving the second fluid adhesion inner surface 22 away from the connection channel 24, even in the presence of maximum perturbation, the main flow will not be able to adhere completely to the second fluid adhesion inner surface 22 itself. There will thus be a partialization of the deviation of the flow as a function of the distance between the second fluid adhesion inner surface 22 and the connection channel 24.

Another way of obtaining a partial deviation of the main flow can be seen in FIG. 6. Indeed, a partialization of the position of the mobile wall 34, in terms of angle formed with respect to the first fluid adhesion inner surface 20, can create a partial deviation of the main flow from such a first fluid adhesion inner surface 20 to the second fluid adhesion inner surface 22.

Figure 7:
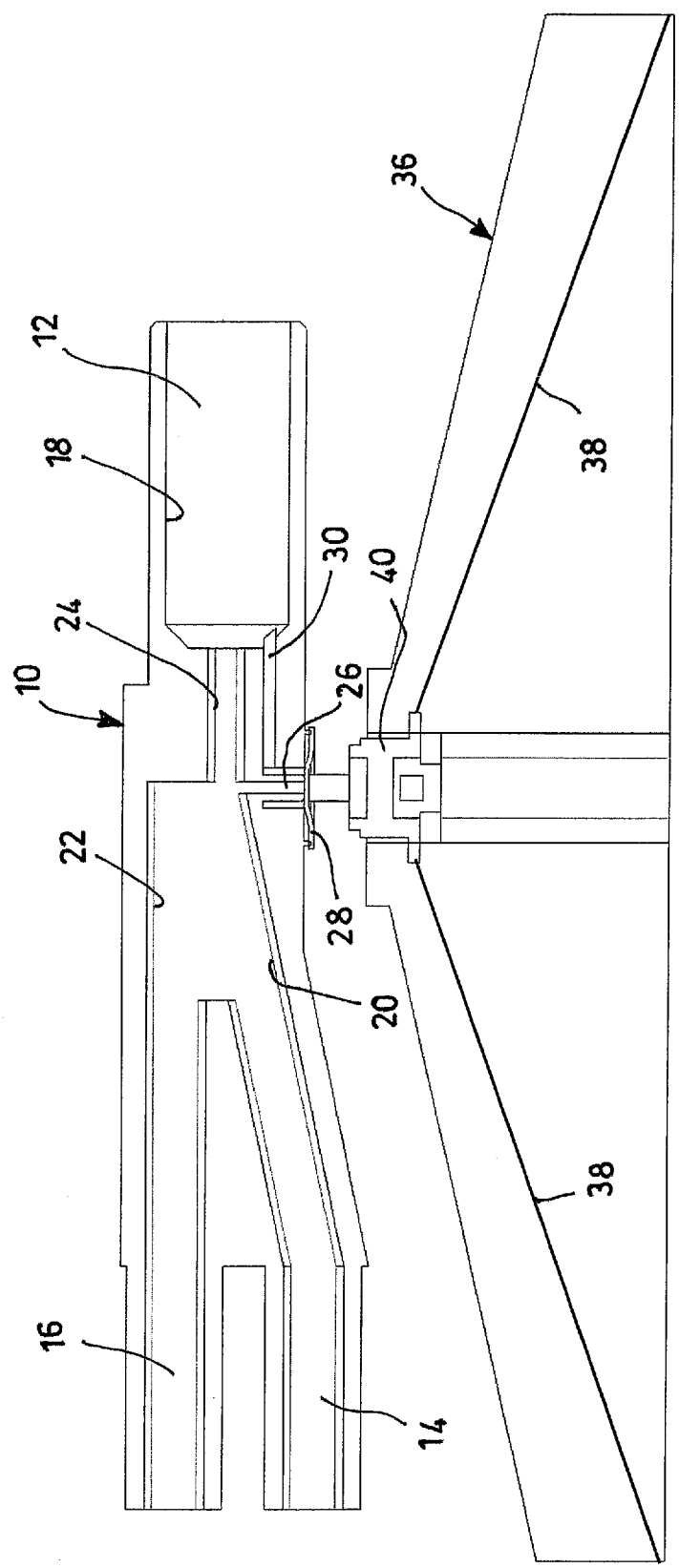
FIG. 7 is a schematic view of the fluidic part of a total isolation diverter valve according to the present invention, provided with a respective actuator device.

FIG. 7 shows an advantageous embodiment of the actuation stage of the total isolation diverter valve according to the present invention. Indeed, with a compact and efficient fluidic part, it is equally advantageous to apply an actuator device 36 at least partially manufactured with a shape memory alloy to the perturbation device. One of the possible configurations of the actuator device 36 is illustrated in FIG. 7 and is applied to the isolation membrane 28 of the monostable valve. However, the actuator device 36 at least partially manufactured with a shape memory alloy, arranged outside of the valve body 10, can also be applied to the other embodiments of the valve.

The actuator device 36 is provided with a wire 38 manufactured with a shape memory alloy. The wire 38, passed through by an electric current, by the Joule effect reaches its phase transition temperature. The resulting deformation (shortening) applies a traction force on a plunger 40 operatively connected to the isolation membrane 28. The linear movement of the plunger 40 determines the opening of the isolation membrane 28, thus placing the perturbation orifice 26 in communication with the secondary inlet conduit 30 for the perturbation fluid. The pressurized fluid that flows from the secondary inlet conduit 30 for the perturbation fluid to the perturbation orifice 26 perturbs the main or preferential adhesion surface 20, deviating the flow on the secondary adhesion surface 22.

It has thus been seen that the total isolation diverter valve according to the present invention achieves the purposes outlined earlier, in particular obtaining the following advantages:
  absolute hygiene of the valve, since the main conduits engaged by the fluids have no additional component necessary for the deviation of the flow or, in other words, the valve is completely "empty" on the inside;
  ability to manage high hydraulic powers with very low actuation forces (in this case "perturbation" forces);
  high deviation speed of the flow, particularly in the case of high hydraulic powers;
  reliability of the valve, since the deviation of the main flow, even for high hydraulic powers, is linked only to a physical effect and not to additional mechanisms and/or devices like levers, pistons or dividing walls that could over time be subject to wear or malfunction;
  possibility of minimizing the size and weight of the valve even for the management of high hydraulic powers;
  possibility of indirectly obtaining, in addition to the diverting of the flow, a mixing between a liquid and air.

Moreover, considering the case in which the main fluid is a liquid and the perturbation scheme that makes the Venturi effect intervene, an indirect characteristic that is obtained (in certain interesting cases, especially in the management of emulsified beverages like for example foamed milk for the preparation of cappuccino) is that of being able to encapsulate air inside the liquid directly in the body of the diverter valve.

Finally, through a suitable design of the geometry of the valve it is also possible to encapsulate air inside the liquid, sucking it from one of the two main fluid outlet conduits 14 or 16 that at that precise moment is not engaged by the crossing of the liquid. Therefore, the diverter valve function is also added to with the possibility of having, for the liquids that allow it, also the emulsifying valve function.

The total isolation diverter valve of the present invention thus conceived can in any case undergo numerous modifications and variants, all of which are covered by the same inventive concept; moreover, all of the details can be replaced by technically equivalent elements. In practice, the materials used, as well as the shapes and sizes, can be whatever according to the technical requirements.

The scope of protection of the invention is therefore defined by the attached claims.

The invention claimed is:

1. Total isolation diverter valve comprising a valve body having a main fluid inlet conduit for inletting a fluid, a first fluid outlet conduit for outletting the fluid and at least one second fluid outlet conduit for outletting the fluid, wherein the first fluid outlet conduit is provided with a first fluid adhesion inner surface and the second fluid outlet conduit is provided with a second fluid adhesion inner surface, a connection channel interposed between the main fluid inlet conduit and said first and second fluid outlet conduits, the connection channel including at least one perturbation device configured so as to cause a deviation of the fluid flow from said first fluid outlet conduit to said second fluid outlet conduit or vice-versa by exploiting a physical effect called Coanda effect, the perturbation device comprising:
  a first perturbation orifice adjacent to said first fluid adhesion inner surface; and
  at least one opening/closing element configured to open and sealingly close the first perturbation orifice,
  the perturbation device being provided with an actuator arranged outside the valve body and comprising a wire manufactured with a shape memory alloy, said wire being configured to deform when an electric current is passed therethrough and being configured to move a plunger operatively connected to said at least one opening/closing element, the movement of said plunger determining the opening of said at least one opening/closing element.

2. Valve according to claim 1, characterized in that said first perturbation orifice is interposed between the main fluid inlet conduit and the first fluid outlet conduit and develops along a direction substantially orthogonal to a development direction of said connection channel.

3. Valve according to claim 1, characterized in that the perturbation device comprises a second perturbation orifice, wherein the first perturbation orifice is interposed between the main fluid inlet conduit and the first fluid outlet conduit and faces the first fluid adhesion inner surface, whereas the second perturbation orifice is interposed between said main fluid inlet conduit and the second fluid outlet conduit and faces the second fluid adhesion inner surface.

4. Valve according to claim 3, characterized in that said first perturbation orifice and said second perturbation orifice develop along a direction substantially orthogonal to the development direction of the connection channel and are arranged along a common axis.

5. Valve according to claim 1, characterized in that said at least one opening/closing element comprises an isolation membrane manufactured with an elastic material, configured for opening and closing a respective perturbation orifice.

6. Valve according to claim 5, characterized in that the perturbation device further comprises at least one secondary fluid inlet conduit for a perturbation fluid, interposed between the main fluid inlet conduit and a respective isolation membrane, wherein said secondary fluid inlet conduit for the perturbation fluid is selectively placed in fluid communication with a respective perturbation orifice through the respective isolation membrane, and wherein a minimal part of the fluid coming from the main fluid inlet conduit, going through the secondary inlet conduit under pressure and flowing through the respective perturbation orifice, generates a flow perturbation by actuating the respective isolation membrane.

7. Valve according to claim 1, characterized in that said at least one opening/closing element consists of a plate movable with reciprocating motion along the direction of development of the respective perturbation orifice, wherein the deviation of the fluid flow from said first fluid outlet conduit to said second fluid outlet conduit or vice-versa is achieved through an air flow coming from outside the valve through said perturbation orifice when the respective plate is in the open configuration.

8. Valve according to claim 1, characterized in that the perturbation device is provided with an actuator device arranged outside the valve body and manufactured at least partially with a shape memory alloy.

9. Valve according to claim 1, characterized in that the perturbation device can be operated for proportionally controlling the deviation of the fluid flow from the first fluid outlet conduit to the second fluid outlet conduit or vice-versa, so as to partially and progressively deviate the amount of fluid from said first fluid outlet conduit to said second fluid outlet conduit or vice-versa.

10. A total isolation diverter valve comprising:
a valve body having a main fluid inlet conduit for inletting a fluid, a first fluid outlet conduit for outletting the fluid and at least one second fluid outlet conduit for outletting the fluid, wherein the first fluid outlet conduit includes a first fluid adhesion inner surface and the second fluid outlet conduit includes a second fluid adhesion inner surface, and a connection channel interposed between the main fluid inlet conduit and said first and second fluid outlet conduits, the connection channel being configured so as to cause a deviation of the fluid flow from said first fluid outlet conduit to said second fluid outlet conduit or vice-versa via a Coanda effect;
the valve body further including:
a first perturbation orifice adjacent to said first fluid adhesion inner surface;
at least one opening/closing element configured to open and sealingly close the first perturbation orifice; and
an actuator arranged outside the valve body and comprising a wire formed of a shape memory alloy, said wire being configured to deform when an electric current is passed therethrough and being configured to move a plunger operatively connected to said at least one opening/closing element, the movement of said plunger determining the opening of said at least one opening/closing element.

11. The valve according to claim 10, characterized in that said first perturbation orifice is interposed between the main fluid inlet conduit and the first fluid outlet conduit and develops along a direction substantially orthogonal to a development direction of said connection channel.

12. The valve according to claim 10, further comprising a second perturbation orifice, wherein the first perturbation orifice is interposed between the main fluid inlet conduit and the first fluid outlet conduit and faces the first fluid adhesion inner surface, whereas the second perturbation orifice is interposed between said main fluid inlet conduit and the second fluid outlet conduit and faces the second fluid adhesion inner surface.

13. The valve according to claim 12, characterized in that said first perturbation orifice and said second perturbation orifice develop along a direction substantially orthogonal to the development direction of the connection channel and are arranged along a common axis.

14. The valve according to claim 10, characterized in that said at least one opening/closing element comprises an isolation membrane manufactured with an elastic material, configured for opening and closing the first perturbation orifice.

15. The valve according to claim 14, further including at least one secondary fluid inlet conduit for a perturbation fluid, interposed between the main fluid inlet conduit and a respective isolation membrane, wherein said secondary fluid inlet conduit for the perturbation fluid is selectively placed in fluid communication with a respective perturbation orifice through the respective isolation membrane, and wherein a minimal part of the fluid coming from the main fluid inlet conduit, going through the secondary inlet conduit under pressure and flowing through the respective perturbation orifice, generates a flow perturbation by actuating the respective isolation membrane.

16. The valve according to claim 10, characterized in that said at least one opening/closing element comprises a plate movable with reciprocating motion along the direction of development of the respective perturbation orifice, wherein the deviation of the fluid flow from said first fluid outlet conduit to said second fluid outlet conduit or vice-versa is achieved through an air flow coming from outside the valve through said perturbation orifice when the respective plate is in the open configuration.

17. A total isolation diverter valve comprising:
a valve body having a main fluid inlet conduit for inletting a fluid, a first fluid outlet conduit for outletting the fluid and at least one second fluid outlet conduit for outletting the fluid, wherein the first fluid outlet conduit includes a first fluid adhesion inner surface and the second fluid outlet conduit includes a second fluid adhesion inner surface, a connection channel between the main fluid inlet conduit and said first and second fluid outlet conduits, the connection channel configured to deviate fluid flow from said first fluid outlet conduit to said second fluid outlet conduit or vice-versa via a Coanda effect, a first perturbation orifice adjacent to said first fluid adhesion inner surface, at least one membrane configured to open and sealingly close the first perturbation orifice;

a wire external to the valve body, said wire being configured to deform when subjected to an electric current to cause movement of a plunger operatively connected to said at least one membrane, the movement of the plunger determining the opening of said at least one membrane.

18. The valve according to claim 17, wherein the wire comprises a shape memory alloy.

* * * * *